(12) United States Patent
Hautvast et al.

(10) Patent No.: US 10,322,299 B2
(45) Date of Patent: Jun. 18, 2019

(54) SYSTEM FOR PERFORMING A THERAPEUTIC PROCEDURE

(71) Applicant: KONINKLIJKE PHILIPS N.V., Eindhoven (NL)

(72) Inventors: Guillaume Leopold Theodorus Hautvast, Veldhoven (NL); Dirk Binnekamp, Borne (NL)

(73) Assignee: Koninklijke Philips N.V., Eindhoven (NL)

(*) Notice: Subject to any disclaimer, the term of this patent is extended or adjusted under 35 U.S.C. 154(b) by 180 days.

(21) Appl. No.: 15/118,107

(22) PCT Filed: Feb. 17, 2015

(86) PCT No.: PCT/EP2015/053254
§ 371 (c)(1),
(2) Date: Aug. 11, 2016

(87) PCT Pub. No.: WO2015/128218
PCT Pub. Date: Sep. 3, 2015

(65) Prior Publication Data
US 2017/0165503 A1 Jun. 15, 2017

(30) Foreign Application Priority Data

Feb. 27, 2014 (EP) .................................... 14156927
Oct. 24, 2014 (EP) .................................... 14190237

(51) Int. Cl.
*A61N 5/10* (2006.01)
*A61B 34/20* (2016.01)

(52) U.S. Cl.
CPC ............ *A61N 5/1048* (2013.01); *A61B 34/20* (2016.02); *A61N 5/1007* (2013.01);
(Continued)

(58) Field of Classification Search
CPC ................ A61N 5/1048; A61N 5/1007; A61N 2005/1008; A61B 34/20; A61B 2034/2061
See application file for complete search history.

(56) References Cited

U.S. PATENT DOCUMENTS

2007/0265503 A1  11/2007  Schlesinger et al.
2009/0287092 A1* 11/2009  Leo .......................... A61B 5/00
                                                          600/474

(Continued)

OTHER PUBLICATIONS

Yu, F.T.S., et al., "Fiber Optic Sensors" Marcel Dekker, Inc. (2002), Chapter 4.

(Continued)

*Primary Examiner* — Christine H Matthews
*Assistant Examiner* — Joshua Daryl D Lannu (57) ABSTRACT

When performing a therapeutic procedure, like a high dose rate (HDR) brachytherapy, an elongate introduction element is introduced into a body, a temperature is determined along the introduction element, and it is determined which part of the introduction element is within the body based on the determined temperature. A therapeutic procedure is performed by using the introduction element depending on the determination which part of the introduction element is within the body. This can ensure that the therapeutic procedure is only performed within the body, thereby reducing the likelihood of involuntary affecting, for instance, a patient's outer skin, especially by ionizing radiation which may be used during a HDR brachytherapy.

16 Claims, 6 Drawing Sheets

(52) U.S. Cl.
CPC .... *A61N 5/1065* (2013.01); *A61B 2034/2061* (2016.02); *A61N 2005/1008* (2013.01)

(56) References Cited

U.S. PATENT DOCUMENTS

| | | |
|---|---|---|
| 2012/0197097 A1 | 8/2012 | Chan et al. |
| 2013/0204072 A1* | 8/2013 | Verard ................ A61N 5/1027 600/8 |
| 2014/0005465 A1 | 1/2014 | Ribbing |
| 2014/0206988 A1* | 7/2014 | Ramachandran ........ G01K 3/14 600/424 |
| 2014/0303486 A1* | 10/2014 | Baumgartner ..... A61B 19/5244 600/414 |
| 2015/0141764 A1 | 5/2015 | Harks |

OTHER PUBLICATIONS

Venselaar, J., et al., "Practical Guide to Quality Control of Brachytherapy Equipment", European Society for Therapeutic Radiology and Oncology (2004).

Lee, K.K.C., et al., Temperature-compensated fiber-optic 3D shape sensor based on femtosecond laster direct-written Bragg grating saveguides, Proc. SPIE 8972, Frontiers in Ultrafast Optics, Biomedical, Scientific and Industrial Applications XIV, 2014.

* cited by examiner

SYSTEM FOR PERFORMING A THERAPEUTIC PROCEDURE

CROSS-REFERENCE TO PRIOR APPLICATIONS

This application is the U.S. National Phase application under 35 U.S.C. § 371 of International Application Serial No. PCT/EP2015/053254, filed on Feb. 17, 2015, which claims the benefit of European Patent Application No. 14190237.9, filed on Oct. 24, 2014 and European Patent Application No. 14156927.7, filed on Feb. 27, 2014. These applications are hereby incorporated by reference herein.

FIELD OF THE INVENTION

The invention relates to a system, method and computer program for performing a therapeutic procedure.

BACKGROUND OF THE INVENTION

A system for performing a therapeutic procedure is, for instance, a high dose rate (HDR) brachytherapy system. A HDR brachytherapy system comprises a brachytherapy catheter, which is introduced into the object to be treated like a prostate of a patient. Within the brachytherapy catheter a radioactive radiation source is moved to different dwell positions, at which the radioactive radiation source is located for a respective dwell time, wherein the object is treated by radioactive radiation emitted by the radioactive radiation source at the different dwell positions for the respective dwell times.

During the movement of the radioactive radiation source to the different dwell positions it can be difficult to know whether the respective dwell position within the brachytherapy catheter is within the patient or outside the patient. If a dwell position, at which the radioactive radiation source is located for a dwell time, is outside of the patient, the patient's outer skin and the environment, especially medical personnel performing the HDR brachytherapy procedure, may be affected by the radioactive radiation.

SUMMARY OF THE INVENTION

It is an object of the present invention to provide a system, method and computer program for performing a therapeutic procedure, wherein the likelihood of involuntary affecting persons by the therapeutic procedure can be reduced.

In a first aspect of the present invention a system for performing a therapeutic procedure is presented, wherein the system comprises:
  an elongate introduction element for being introduced into a body,
  a temperature determination unit for determining a temperature along the introduction element,
  an inner part determination unit for determining which part of the introduction element is within the body based on the determined temperature, and
  a therapeutic procedure performing unit for performing the therapeutic procedure by using the introduction element depending on the determination which part of the introduction element is within the body.

Since the temperature along the introduction element is determined and used for determining which part of the introduction element is within the body and since the therapeutic procedure using the introduction element is performed depending on the determination which part of the introduction element is within the body, the therapeutic procedure can be performed such that it is only performed within the body. This allows for a reduction of the likelihood of involuntary affecting, for instance, a patient's outer skin and the environment, especially medical personnel, by the therapeutic procedure.

The elongate introduction element is preferentially a catheter, especially a brachytherapy catheter. The temperature determination unit is preferentially adapted to determine the temperature along the introduction element in real-time such that also the determination which part of the introduction element is within the body can be performed in real-time.

In an embodiment the introduction element is a catheter and the therapeutic procedure performing unit comprises a) a moving unit for moving a radiation source to a dwell position for treating the body at the dwell position within the catheter, and b) a brachytherapy control unit for controlling the moving unit such that the dwell position is within the part of the catheter which has been determined as being within the body. The radiation source, which is preferentially a radioactive radiation source, is preferentially only stationary at the dwell position, wherein it is assumed that the therapeutic procedure is only performed at the dwell position, because at this position the radiation emitted by the radiation source is present for a time being long enough for having a therapeutic effect. Thus, by controlling the moving unit such that the dwell position is within the part of the catheter, which has been determined as being within the body, it can be ensured that the therapeutic procedure is only performed within the body, thereby reducing the likelihood that, for instance, a patient's outer skin and the environment, especially medical personnel, are affected by the radiation emitted by the radiation source. The catheter and the therapeutic procedure performing unit are preferentially adapted to perform a HDR brachytherapy.

The introduction element preferentially comprises an optical fiber for generating optical signals being indicative of the temperature along the introduction element, wherein the temperature determination unit is preferentially adapted to determine the temperature along the introduction element based on the generated optical signals. By determining the temperature along the introduction element based on optical signals, the temperature can be determined very accurately. Moreover, by using fiber optic sensing the temperature can be determined in a very unobtrusive way, i.e. the user does not need to handle a further device for measuring the temperature.

Preferentially, the optical fiber is equipped with optical temperature sensors, wherein the measuring process involves processing the reflected light that is received from the optical temperature sensors after emitting light into the optical fiber. In an embodiment the optical temperature sensors are fiber Bragg gratings, which reflect a particular part of the incoming spectrum as function of temperature-dependent strain. The reflected light, i.e. the generated optical signals, can then be used by the temperature determination unit for determining the temperature along the introduction element. The introduction element preferentially comprises several optical fibers, especially three of more optical fibers, wherein each optical fiber may be equipped with fiber Bragg gratings and the optical signals of all optical fibers may be used for determining the temperature along the introduction element. For more details regarding the fiber optic temperature sensing reference is made to, for instance, the book "Fiber Optic Sensors" edited by F. T.

S. Yu and S. Yin, Marcel Dekker, Inc. (2002), especially chapter 4 of this book, which is herewith incorporated by reference.

The inner part determination unit is preferentially adapted to determine which part of the introduction element is within the body by determining an increase or decrease of the temperature along the introduction element. For instance, temperature gradients can be determined along the length of the introduction element and thresholded, in order to determine which part of the introduction element is within the body. Since it is assumed that the temperature within the body is larger (for instance, about 37 degrees Celsius) and outside the body smaller (for instance, about 20 degrees Celsius), by determining an increase or decrease of the temperature along the introduction element, for example, by determining spatial gradients and by thresholding the spatial gradients, the location along the introduction element, at which the introduction element enters the body, and correspondingly the part of the introduction element within the body and the part of the introduction element outside the body can reliably be determined.

In an embodiment the inner part determination unit is adapted to determine which part of the introduction element is within the body by modeling thermodynamic properties of the body and/or of the environment and/or of the introduction element and by using the determined temperature along the introduction element. By not only considering the determined temperature along the introduction element, but by additionally considering thermodynamic properties of the body and/or of the environment and/or of the introduction element, the accuracy of determining which part of the introduction element is within the body can be further increased.

The system may further comprise a depth determination unit for determining the depth of the introduction element within the body based on the determined inner part of the introduction element, wherein the determined depth may be shown to the user. Moreover, the depth determination unit may be further adapted to determine a deviation of the determined depth of the introduction element with a predefined depth and to indicate the deviation. The predefined depth can be a previous depth which has been determined earlier, in order to determine whether the depth has changed in time. The predefined depth can also be, for instance, user defined. If there is a deviation, especially a deviation being larger than a predefined deviation threshold, an alarm may be generated to trigger the user. Alternatively or in addition, the therapeutic procedure may be stopped, i.e., for instance, in the case of HDR brachytherapy the radiation source may be retracted from the catheter, if the deviation indicates that the catheter has been moved too much during radiation delivery.

The system may further comprise a target depth providing unit for providing a target depth of the introduction element and a guidance information generation unit for generating guidance information being indicative of a movement of the introduction element, which would allow the introduction element to reach the target depth, based on the provided target depth and the determined depth of the introduction element. The guidance information can indicate, for instance, that the introduction element should be moved further into the body by a certain distance. This guidance information may be given in real-time such that the user can be guided by the guidance information while introducing the introduction element into the body.

In an embodiment the system further comprises a) a position determination unit for determining the position of the introduction element within the body, b) a body image providing unit for providing a body image, wherein the provided body image is registered with the determined position of the introduction element, and c) an introduction element image generation unit for generating an introduction element image showing a representation of the introduction element within the object image based on the determined position of the introduction element within the body and the body image. Thus, the position of the introduction element relative to the body can be shown, especially in real-time, thereby allowing a user to monitor the introduction process. In an embodiment the introduction element image generation unit is adapted to generate the introduction element image such that only a representation of the inner part or outer part of the introduction element is shown based on the determination which part of the introduction element is within the body. However, in another embodiment also the entire introduction element may be represented in the introduction element image.

The introduction element preferentially comprises an optical shape sensing fiber for generating optical shape sensing signals being indicative of the position of the introduction element within the body, wherein the position determination unit is adapted to determine the position of the introduction element within the body based on the generated optical shape sensing signals. Since the position of the introduction element is determined based on optical shape sensing signals, the position can be determined very accurately in a for a user very unobtrusive way, i.e. without requiring the user to use additional position detection means like electromagnetic position detection means. The optical shape sensing fiber preferentially comprises fiber Bragg gratings for generating optical signals, i.e. optical shape sensing signals, being indicative of the strain at the locations at which the fiber Bragg gratings are present, wherein the strain along the optical fiber may be integrated for determining the shape and together with a known position of a point or segment of the introduction element the position of the entire introduction element. The introduction element preferentially comprises several optical fibers, especially three of more optical fibers, wherein each optical fiber may be equipped with fiber Bragg gratings and the optical signals of all optical fibers may be used for determining the position of the introduction element, i.e. the position of each portion of the introduction element. For more details regarding the fiber optic position sensing reference is made to, for instance, the above mentioned book "Fiber Optic Sensors" edited by F. T. S. Yu and S. Yin, Marcel Dekker, Inc. (2002), especially chapter 4 of this book, which is herewith incorporated by reference. Moreover, the same optical shape sensing signals may also be used for determining the temperature along the length of the introduction element such that the position determination functionality and the temperature determination functionality can be provided in a single compact device.

The body image providing unit is preferentially adapted to provide the position of the introduction location, at which the introduction element is introduced into the body, relative to the provided body image and to register the body image with the position of the introduction element based on the provided position of the introduction location and the proximal end of the determined inner part of the introduction element. Thus, the body image may be registered with the position of the introduction element in a relatively simple way by using the proximal end of the determined inner part of the introduction element, which defines the position at which the introduction element enters the body. The determination which part of the introduction element is within the body may therefore not only be used for controlling the therapeutic process, but also for registering the position of the introduction element with the provided body image. Also this leads to a very compact system, which can be handled by the user in a relatively simple way. The position of the introduction location relative to the provided body image may be provided by the body image providing unit by using image processing algorithms, especially segmentation algorithms, for detecting the introduction location within the body image.

In a further aspect of the present invention a method for performing a therapeutic procedure is presented, wherein the method comprises:

determining a temperature along an introduction element, which has been introduced into a body, by a temperature determination unit, determining which part of the introduction element is within the body based on the determined temperature by an inner part determination unit, performing the therapeutic procedure by using the introduction element depending on the determination which part of the introduction element is within the body by a therapeutic procedure performing unit.

In a further aspect of the present invention a computer program for causing a system to carry out the steps of the above mentioned method, when the computer program is run on a computer controlling the system.

It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
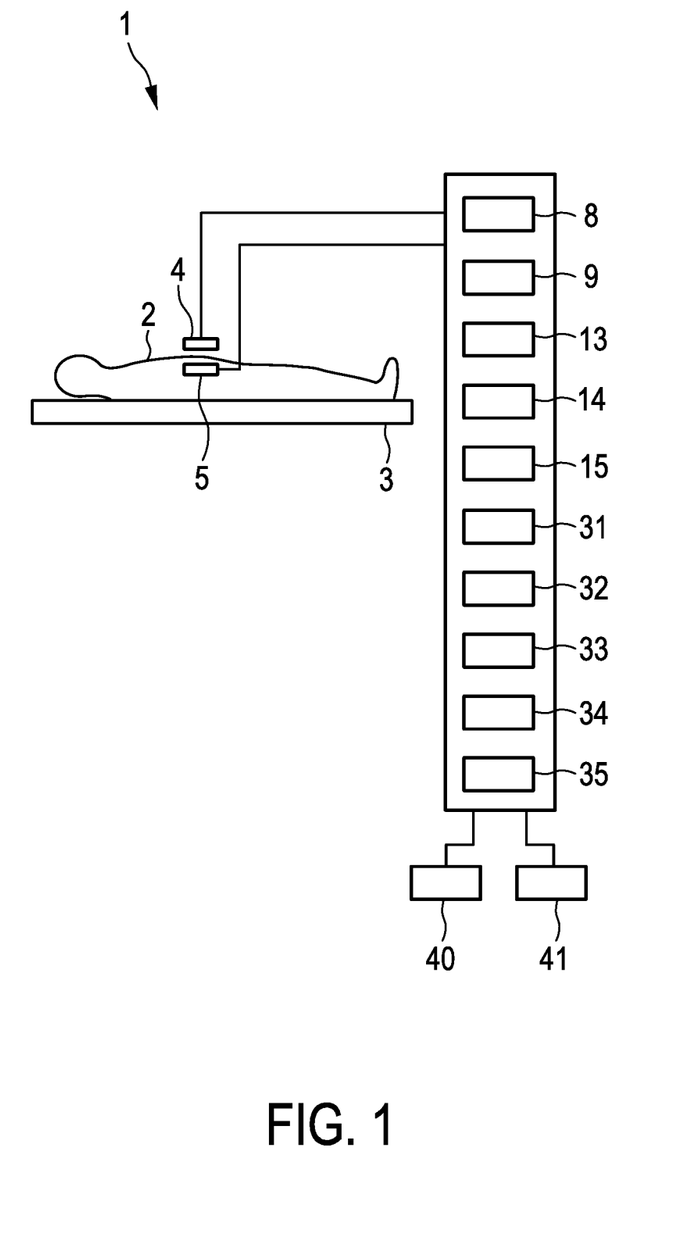
FIG. 1 shows schematically and exemplarily an embodiment of a system for performing a therapeutic procedure.

FIG. 1 shows schematically and exemplarily a system for performing a therapeutic procedure. In this embodiment the system 1 is a brachytherapy system for applying a brachytherapy to a body 2 of a person lying on a support means 3 like a table. The brachytherapy system 1 comprises a placing unit 5 for placing radiation sources close to a target region within the body 2 for directing radiation emitted by the radiation sources to the target region. The placing unit 5 is exemplarily and schematically shown in more detail in FIG. 2.

Figure 2:
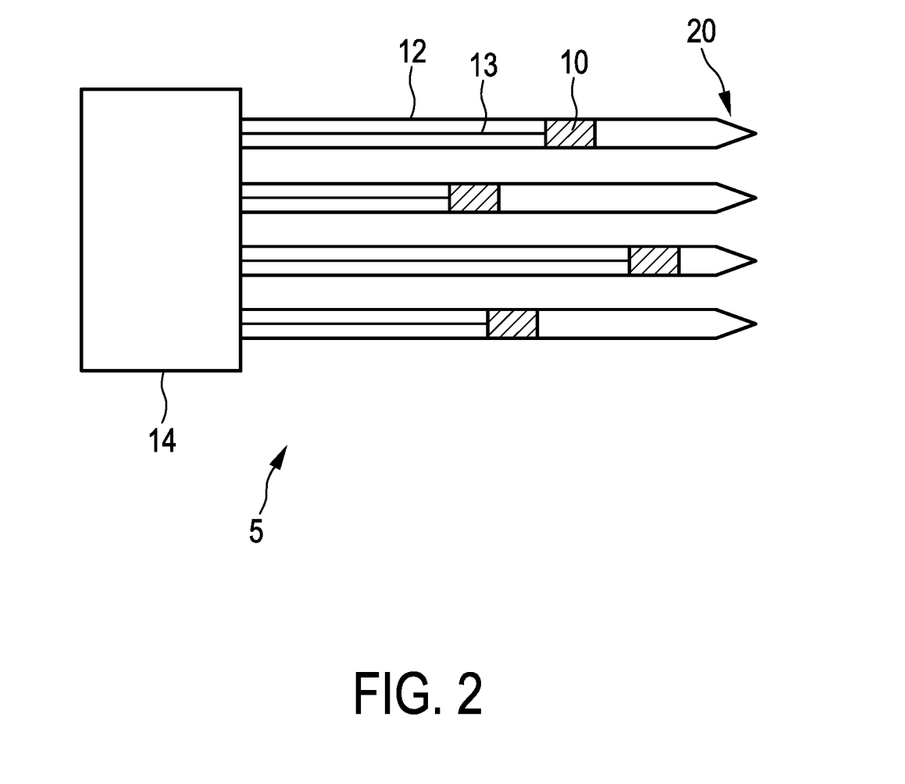
FIG. 2 shows schematically and exemplarily introduction elements of the system to be introduced into a body for performing the therapeutic procedure.

The placing unit 5 comprises several elongate introduction elements 12, which in this embodiment are catheters, with tips 20 for being introduced into the body 2. The placing unit 5 further comprises several navigation elements 13 being drive wires to which the radiation sources 10 are attached, wherein a respective drive wire 13 can be moved within a respective catheter 12 for placing a respective radiation source 10 at a desired dwell position. The catheters 12 with the drive wires 13 are attached to a motor unit 14 comprising several motors for moving the drive wires 13 in a forward direction and in a backward direction for placing the radiation sources 10 at the desired dwell positions. The radiation sources 10 are preferentially radioactive radiation sources emitting radioactive radiation like Ir-192.

The placing unit can comprise further elements for assisting in placing the radiation sources at the desired dwell positions within the body. For instance, the placing unit can comprise a template which can be used for inserting the catheters in a more uniform configuration into the body.

Figure 3:
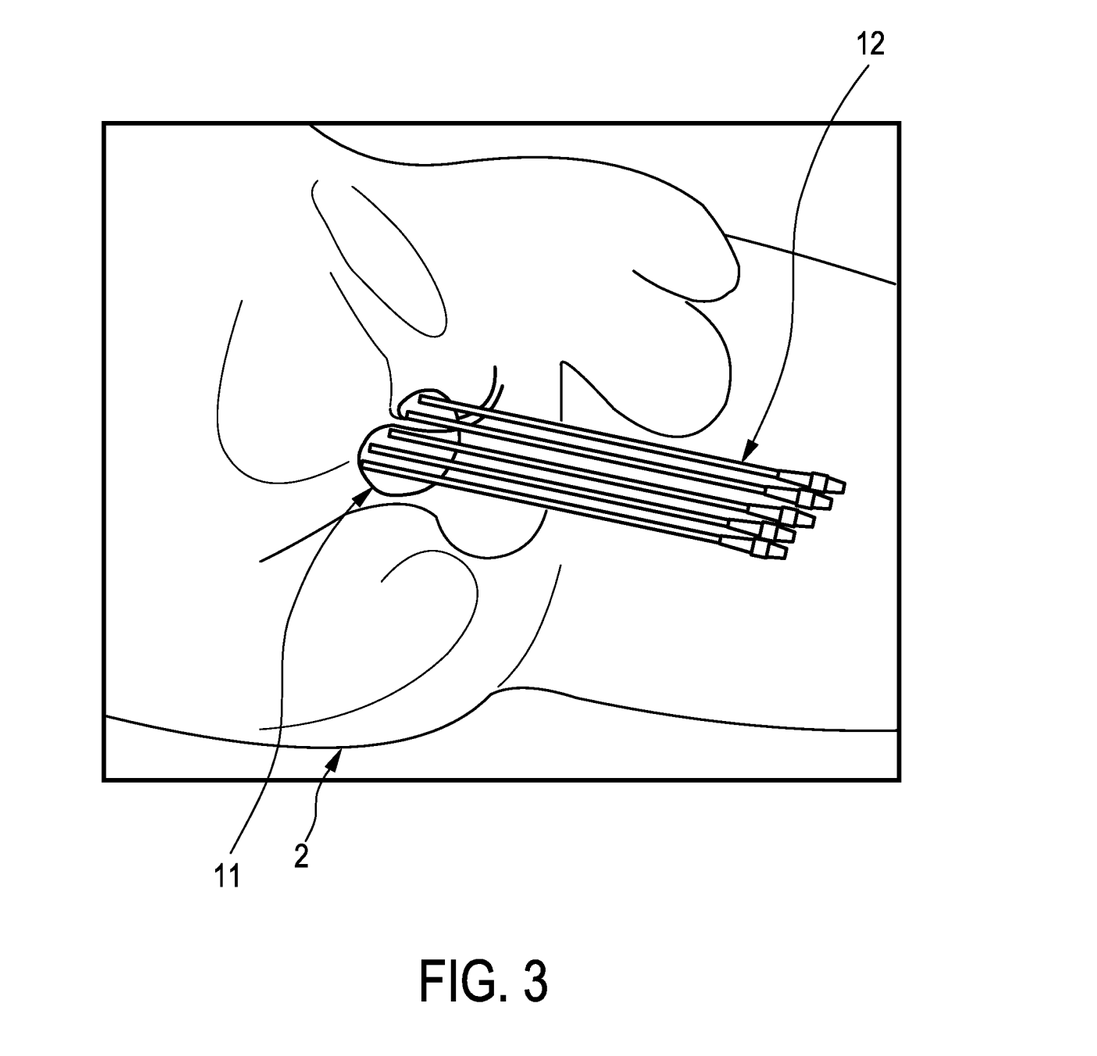
FIG. 3 illustrates schematically and exemplarily a possible arrangement of the introduction elements after having been introduced into the body.

In this embodiment the system 1 is adapted to treat a target region, which is preferentially a tumor region, in a prostate. In order to place the radiation sources close to the target region, they can be placed adjacent to or within the target region. FIG. 3 shows schematically and exemplarily a possible arrangement of the catheters 12 of the placing unit 5 within the prostate 11.

The system 1 further comprises an imaging unit 4, 8 being, in this embodiment, an ultrasound unit. The ultrasound unit comprises an ultrasound probe 4 and an ultrasound control unit 8. The ultrasound probe 4 may be placed on the outside surface of the body 2 as schematically and exemplarily illustrated in FIG. 1, or the ultrasound probe may be arranged within the body 2, in order to generate an image of the body 2, especially of the target region 11. For instance, the ultrasound probe may be a transrectal ultrasound probe. The generated image can be shown to a user on a display 41, in order to guide the user while introducing the catheters 12 into the body 2. In another embodiment the imaging unit can be another kind of imaging device like a magnetic resonance imaging device. Since the imaging unit 4, 8 provides the body image, the imaging unit 4, 8 can be regarded as being a body image providing unit.

Each catheter 12 comprises an optical shape sensing fiber. In particular, as schematically and exemplarily shown in FIG. 4, each catheter 12 may comprise three optical shape sensing fibers 17 within an outer wall 16, wherein these three optical shape sensing fibers 17 may be angularly equidistantly distributed, i.e. they may have an angular distance to each other of 120 degrees. The system 1 further comprises an optical shape sensing control unit 9 for generating optical shape sensing signals by using the optical shape sensing fibers 17, wherein the generated optical shape sensing signals are provided to a temperature determination unit 13 for determining the temperature along the length of the respective catheter 12 based on the generated optical shape sensing signals.

The system further comprises an inner part determination unit 14 for determining which part of the respective catheter 12 is within the body 2 based on the determined temperature. The inner part determination unit 14 can be adapted to determine which part of the respective catheter 12 is within the body 2 by, for instance, thresholding the measured temperature or by calculating a spatial temperature gradient and/or a temporal temperature gradient along the respective catheter 12 and thresholding the respective temperature gradient. The thresholds may be static thresholds, i.e. constant thresholds, or they may be dynamic thresholds, i.e. they may be modified over time. Rules can be provided, which define the inside/outside position along the respective catheter based on the temperature determined along the respective catheter. The rules can define thresholds for thresholding temperature values and/or spatial temperature gradients and/or temporal temperature gradients and how the results of these thresholding operations can be combined, in order to determine the inside/outside position along the respective catheter 12. It can be defined that a position, at which a spatial temperature gradient is larger than a predefined threshold, indicates an inside/outside position. Moreover, it can be defined that a position, at which a temporal temperature gradient is larger than a predefined threshold and therefore indicates a sudden drop or increase in temperature, indicates an inside/outside position, especially while the respective catheter 12 is inserted into or retracted from the body 2. The rules, especially the thresholds, can be determined by calibration measurements, wherein the inside/outside position along the respective catheter is known and the rules, especially the thresholds, are determined such that, given a known temperature distribution along the respective catheter, the known inside/outside position results.

The inner part determination unit 14 can also be adapted to determine which part of the respective catheter 12 is within the body 2 and which part of the respective catheter 12 is outside the body 2 based on the temperature determined along the length of the respective catheter 12 by using another technique. In particular, a model considering thermodynamic properties of the body 2, of the environment and/or of the catheters 12 may be used in addition to the temperature determined along the catheters 12. For instance, a model can be used, which involves compartments for inside and outside the body at temperatures of 20 degrees Celsius and 37 degrees Celsius. The respective catheter 12 itself may be modeled as a cylinder with a radius and wall thickness, which is made of a metal with known thermal capacity. This allows for a computation of the heat transfer that is required for the respective optical shape sensing sensor to pick up a change of temperature due to the insertion of the respective catheter 12 into the body 2. This model may then be inverted, in order to allow the inner part determination 14 to determine the position of the transition between inside and outside the body, given the temperature determined along the respective catheter 12. Such a model may also be used to determine the above mentioned thresholds which may be used for thresholding the temperature, the spatial temperature gradient and/or the temporal temperature gradient.

The system 1 further comprises a position determination unit 35 for determining the positions of the catheters 12 within the body based on the generated optical shape sensing signals. Thus, the optical shape sensing signals are not only used for determining the temperature along the length of the respective catheter 12, but also for determining the positions of the catheters 12 within the body 2. In particular, the position determination unit 35 is adapted to determine the shape of the catheters 12 and to determine the positions of each portion of the respective catheter 12 based on the determined respective shape and a known position, i.e. location and orientation, of at least one point of the respective catheter 12. This known position can be determined outside the body by any known means. In an embodiment the point of the respective catheter 12 with the known position is the incision point, i.e. the point where the respective catheter 12 enters the body, wherein the position of this point may be tracked by, for instance, electromagnetic tracking, video tracking or another tracking technique.

The determined positions of the catheters 12 within the body 2 can be registered with the image of the body 2 provided by the imaging unit 4, 8, in order to allow an introduction element image generation unit 34 to generate an introduction element image showing representations of the catheters 12 within the body image based on the determined positions of the catheters 12 and the body image provided by the imaging unit 4, 8. The generated introduction element image can be shown on the display 41, in order to provide guidance for the user while introducing the catheters 12 into the body 2.

Instead of or in addition to generating a current image of the body 2, the imaging unit can be adapted to provide a pre-interventional image, wherein also in this case the determined positions of the catheters 12 within the body 2 can be registered with the image of the body 2 provided by the imaging unit, in order to allow the introduction element image generation unit 34 to generate an introduction element image showing representations of the catheters 12 within the body image based on the determined positions of the catheters 12 and the body image provided by the imaging unit. The generated introduction element image, which in this example is based on the pre-interventional image, can be shown on the display 41, in order to provide guidance for the user while introducing the catheters 12 into the body 2.

The introduction element image generation unit 34 can be adapted to generate representations representing the entire catheters 12. However, the introduction element image generation unit 34 can also be adapted to generate representations representing only the inner parts or only the outer parts of the catheters 12 based on the determination which part of the respective catheter 12 is within the body and which part of the respective catheter 12 is outside the body.

For registering the body image with the determined positions of the catheters 12 the body image providing unit, especially the ultrasound control unit 8, may be adapted to provide the position of the respective introduction location, at which the respective catheter 12 is introduced into the body 2, relative to the provided body image, wherein the registration can be based on the fact that these provided positions of the introduction locations correspond to proximal ends of the parts of the catheters 12, which are inside the body 2. The determination of these parts of the catheters 12 within the body 2 will be explained further below. The position of the introduction location relative to the provided body image may be provided by the body image providing unit by using image processing algorithms, especially segmentation algorithms, for detecting the introduction location within the body image. In other embodiments also other known techniques for registering a determined position of an introduction element like a catheter with an image of the body can be used.

The motor unit 14 and the drive wires 13 can be regarded as being a moving unit for moving the radiation sources 10 to the dwell positions for treating the body 2, especially the target region 11, at the dwell positions within the catheters 12. This moving unit 13, 14 is controlled by a brachytherapy control unit 15 depending on the determination which part of the respective catheter 12 is within the body 2 and which part of the respective catheter 12 is outside the body 2 such that each dwell position is surely within the part of the respective catheter 12 within the body 2, i.e. such that the movement of the radiation sources 10 within the catheters 12 does not halt outside the body 2. The brachytherapy control unit 15, which together with the moving unit 13, 14 can be regarded as being a therapeutic procedure performing unit, is therefore adapted to perform the therapeutic procedure, i.e. the brachytherapy in this embodiment, depending on the determination which part of the respective catheter 12 is within the body 2, especially such that the therapeutic procedure is performed only at the determined inner parts of the catheters 12.

Figure 5:
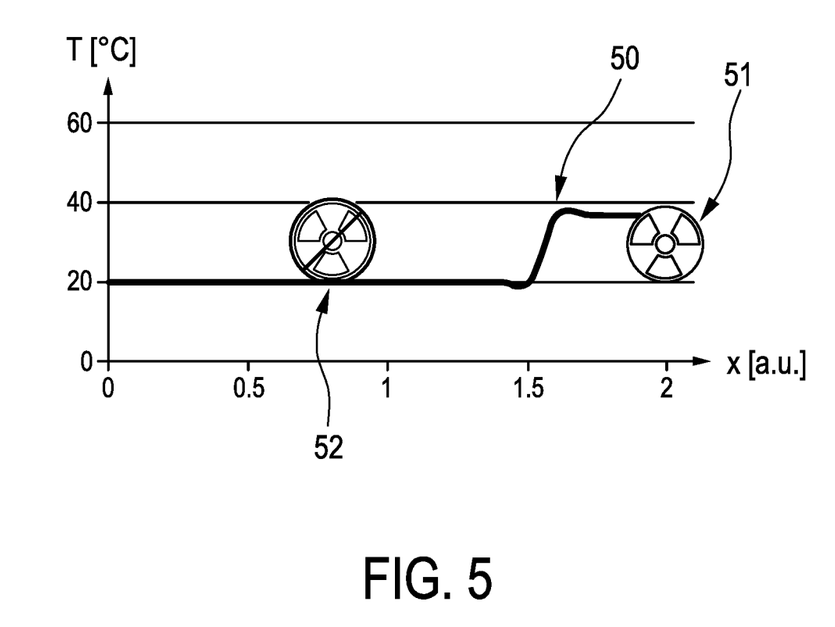
FIG. 5 illustrates schematically and exemplarily a temperature distribution measured along an introduction element.

FIG. 5 schematically and exemplarily shows a measured temperature Tin degrees Celsius along a catheter 12, wherein the different locations along the catheter 12 in arbitrary units are indicated by x in arbitrary units. At a region 50 an increase of the temperature can be observed, which can be detected by the inner part determination unit 14, in order to determine which part of the catheter 12 is within the body 2 and which part of the catheter 12 is outside the body 2. The brachytherapy control unit 15 is adapted such that the dwell positions are only within the body as indicated by the symbol 51 and not outside the body as indicated by the symbol 52.

The system 1 can further comprise a depth determination unit 31 for determining the depth of the respective catheter 12 within the body 2 based on the determined inner part of the respective catheter 12. In particular, the position determination unit 35 is adapted to determine the position of each portion of the respective catheter 12 and the depth determination unit 31 is adapted to determine the depth of the respective catheter 12 based on the determined positions of the portions of the respective catheter 12 and the knowledge which of these portions are within the body 2 as provided by the inner part determination unit 14. The determined depths of the catheters 12 may be shown to the user on the display 41. The depth determination unit 31 can be further adapted to determine a deviation of the determined depths of the catheters 12 with predefined depths and to indicate the deviation. For instance, the predefined depths can be previous depths which have been determined earlier, in order to determine whether the depths have changed in time. The predefined depths can also be, for instance, user defined. If there is a deviation, especially a deviation being larger than a predefined deviation threshold, an alarm may be generated to trigger the user. Thus, the temperature-based segmentation, i.e. the determination which part of the respective catheter 12 is within the body 2 and which part of the respective catheter 12 is outside the body 2 based on the temperature determined along the respective catheter 12, may be used to derive the respective insertion depth, wherein particularly in the case of brachytherapy this may serve as a quality assurance for the treatment, confirming that the catheters 12 are still at the same positions/depths. If this is not the case, an alarm may be generated. The remaining length of the respective catheter outside the body as determined by using the temperature-based segmentation may be reported to the user via the display 41. This outside length may also be used for quality assurance.

The system 1 can further comprise a target depth providing unit 32 for providing a target depth of the respective catheter 12 and a guidance information generation unit 33 for generating guidance information being indicative of a movement of the respective catheter 12, which would allow the respective catheter 12 to reach the target depth, based on the provided target depth and the determined depth of the respective catheter 12. The guidance information can indicate, for instance, that the respective catheter 12 should be moved further into the body 2 by a certain distance. This guidance information may be given in real-time such that the user can be guided by the guidance information while introducing the catheters 12 into the body 2.

The system 1 further comprises an input unit 40 like a keyboard, a computer mouse, a touch pad, et cetera, in order to allow a user to, for instance, input commands into the system 1 like a start command for starting a brachytherapy procedure, a stop command to stopping a brachytherapy procedure, et cetera. The input unit 40 may also be used to input parameters defining the brachytherapy procedure like dwell positions and dwell times. Dwell positions and dwell times may also be automatically determined by the brachytherapy control unit 15 based on, for instance, an image showing the target region and a desired radiation dose, which may be input by the user, to be applied to the target region. Known planning algorithms can be used for determining the dwell times and dwell positions, wherein the brachytherapy control unit can be adapted to control the moving unit 13, 14 in accordance with the provided desired dwell times and dwell positions such that the dwell positions are surely within the parts of the catheters 12, which have been determined as being within the body 2.

Figure 6:
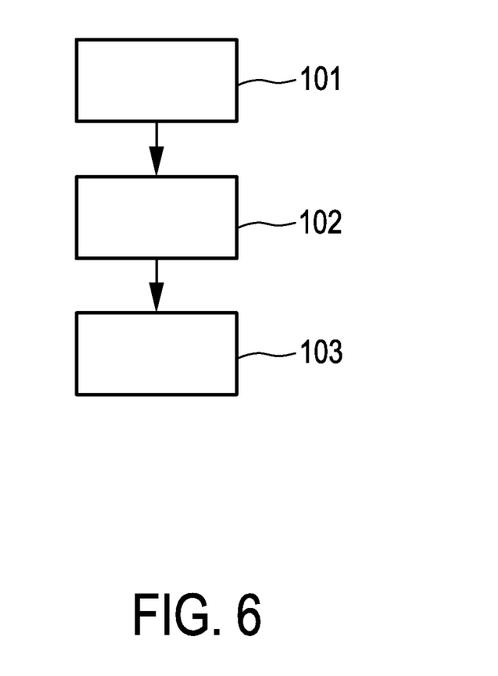
FIG. 6 shows a flowchart exemplarily illustrating an embodiment of a method for performing a therapeutic procedure.

In the following an embodiment of a method for performing a therapeutic procedure will exemplarily be described with reference to a flowchart shown in FIG. 6.

In step 101 the temperature along the respective catheter 12, which has been introduced into the body 2, is determined by the temperature determination unit 13, i.e. the temperature at different locations along the respective catheter 12 is determined by the temperature determination unit 13. In particular, the temperature determination unit 13 is adapted to determine these temperature distributions based on optical shape sensing signals, which have been generated by using the optical fibers 17 of the catheters 12 and the optical shape sensing control unit 9. In step 102 the inner part determination unit 14 determines which part of the respective catheter 12 is within the body 2 and which part of the respective catheter 12 is outside the body 2 based on the respective determined temperature distribution. For instance, the inner part determination unit 14 may calculate temperature gradients along the respective catheter 12 and threshold the temperature gradients, in order to determine which part of the respective catheter 12 is inside the body 2 and which part of the respective catheter 12 is outside the body 2. In step 103 the therapeutic procedure, i.e. in this embodiment the brachytherapy procedure, is performed depending on the determination which part of the respective catheter 12 is within the body 2 and which part of the respective catheter 12 is outside the body 2. In particular, the brachytherapy control unit 15 controls the moving unit 13, 14 such that the dwell positions are surely only within the parts of the catheters 12, which have been determined as being within the body 2, i.e. such that the movement of the radiation sources 10 within the catheters 12 does not halt outside the body 2.

Steps 101 to 103 may be performed in a loop such that continuously the temperature along the catheters 12 is determined and used for determining which part of the respective catheter 12 is within the body 2 and which part of the respective catheter 12 is outside the body 2. This allows the therapeutic procedure performing unit 13, 14, 15 to perform the therapy such that the dwell positions are surely within the parts of the catheters 12, which have been determined as being inside the body 2, even if the depth of the respective catheter 12 within the body 2 changes during the therapeutic procedure.

Figure 4:
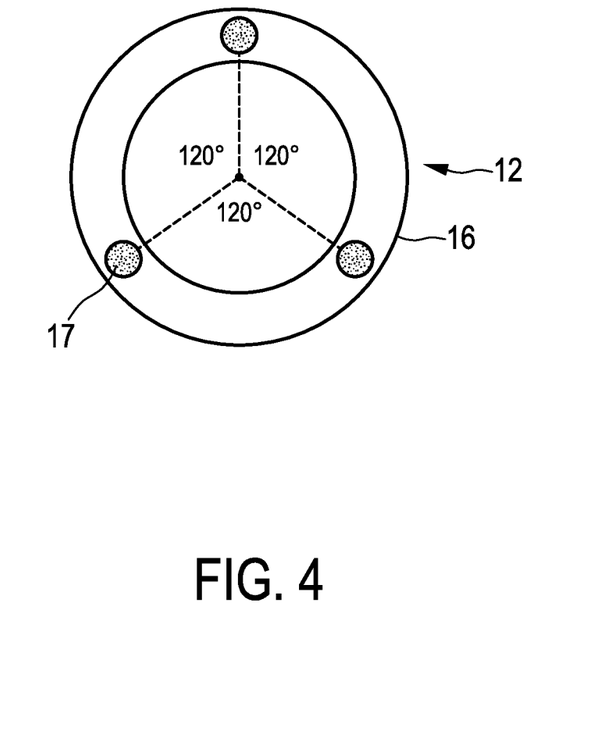
FIG. 4 shows schematically and exemplarily a sectional view of an introduction element.

The optical shape sensing fibers 17 have Bragg gratings, which act as highly selective reflectors, wherein the optical shape sensing fibers 17 are connected to a broadband source and a detector of the optical shape sensing control unit 9. The peak reflected wavelength for each Bragg grating shifts due to changes in strain and temperature such that these shifts can be used to reconstruct the shape and temperature of the respective catheter. In particular, the shape of the entire respective catheter relative to a respective known anchoring location can be reconstructed, in order to determine the position of each portion or section of the respective catheter, and the temperature at different portions or sections along the length of the respective catheter can be determined. For more details regarding the determination of the position of a catheter and of a temperature along a length of a catheter based on optical shape sensing reference is made to, for instance, the above mentioned book "Fiber Optic Sensors" edited by F. T. S. Yu and S. Yin, Marcel Dekker, Inc. (2002), especially chapter 4 of this book, which is herewith incorporated by reference.

Given the temperature along the respective catheter it is possible to detect which part of the respective catheter is inside the body. The fiber optic sensing technology is capable of measuring temperatures in real-time. As the temperature difference between the body and its environment is rather large, the measured temperature will thus quickly increase when inserting the respective catheter.

The temperature-based segmentation of the respective catheter is used to prevent undesired operations. In particular, the brachytherapy, which is preferentially a HDR brachytherapy, is performed such that dwell positions for the radiation source are not outside the body, i.e. the dwell positions are not in the "cold" parts of the respective tracked catheter, which might be regarded as being a HDR dose delivery catheter. The catheters 12 may reside in the body for several days such that the temperature along the respective catheter may be assumed to be in steady state.

The temperature-based segmentation can be used to provide depth guidance during insertion by using, for instance, the above described depth determination unit, target depth providing unit and guidance information generation unit. It is possible to indicate to the user at what depth the respective catheter currently is, as well as provide further guidance based on the current depth derived from the temperature along the respective catheter and the intended target depth. Feedback may be provided on whether to insert the respective catheter further into the body or not.

In HDR brachytherapy a highly radioactive radiation source may be moved through a target lesion using a set of catheters. To guarantee patient safety and treatment efficiency, the radiation dose should not be delivered outside the patient's body. The system described above with reference to FIGS. 1 to 5 actively controls therefore the delivery of the treatment based on temperature sensing along the delivery catheters such that the radioactive radiation source will not dwell, i.e. stop to deliver dose, outside the patient's body. The temperature sensing is achieved by embedding fiber optic sensing in the dose delivery catheters. Given the relatively large difference in temperature, the inner part determination unit can identify which part of the respective catheter is inside/outside the patient's body using relatively straight-forward static criteria like a temperature threshold. For instance, as a temperature threshold the average of the environmental temperature, which might be 20 degrees Celsius, and the body temperature, which might be 37 degrees Celsius, may be used, wherein a part of the respective catheter having a temperature below this temperature threshold can be regarded as being outside of the patient's body and a part of the respective catheter having a temperature above the temperature threshold can be regarded as being within the patient's body. However, more advanced limitations may take into account temperature gradients over time and along the catheter. Moreover, knowledge about properties of the material of the respective catheter may be also used, in order to achieve a further robustness.

If a dwell position is classified as being outside the patient's body, the brachytherapy control unit 15 will control the drive wires 13 via the motor unit 14 to prevent the respective radiation source 10 from dwelling at that position. A dwell time may be in the range of some seconds, for instance, within the range of 1 s to 60 s. However, a dwell time may also be larger or smaller. This autonomous control, which may be integrated in an afterloader, can prevent adverse events.

Although in above described embodiments the introduction element is a catheter, in other embodiments the introduction element can be another element, especially another surgical instrument. Moreover, although in above described embodiments the system for performing a therapeutic procedure is a brachytherapy system, especially a HDR brachytherapy system, in other embodiments the system can also be another system for performing a therapeutic procedure. For instance, it can be a system comprising an elongate surgical instrument like an ablation catheter comprising several ablation elements, which might be ablation electrodes, for applying ablation energy to tissue, wherein a therapeutic procedure performing unit can control the surgical instrument such that the therapeutic procedure like applying the ablation energy is performed only within the body and not outside the body. The system can especially be adapted to be used in the field of minimally invasive surgery (MIS) and image guided interventions and therapy (IGIT).

Although in above described embodiments the temperatures along the lengths of the catheters and the positions of the catheters have been determined by optical shape sensing, in other embodiments the temperatures and the positions can be determined by using other techniques. For instance, the temperatures may be determined by thermistors distributed along the respective catheter or by using fiber optic sensors which are not adapted to determine the position of the respective catheter. The position of the respective catheter may be determined by, for instance, electromagnetic tracking, x-ray tracking et cetera.

Although in the embodiment described above with reference to FIGS. 1 to 3, especially FIG. 2, a placing unit 5 has been described, which comprises several drive wires 13 with attached radiation sources 2, in other embodiments another kind of placing unit may be used. For instance, a single drive wire with a single radiation source may be used, wherein this single drive wire may be consecutively introduced into the different catheters 12. In particular, the radiation source may be driven through an indexer that is connected with the different catheters. For more details regarding this kind of placing the radiation source within the patient reference is made to the "Practical Guide to Quality Control of Brachytherapy Equipment" edited by J. Venselaar and J. Perez-Calatayud, European Society for Therapeutic Radiology and Oncology (2004), which is herewith incorporated by reference.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Determinations like the determination of the temperature and the positions based on the optical shape sensing signals, the determination of the inner parts of the catheters, the determination of the depth of the respective catheter, et cetera and/or the control of the system for performing the therapeutic procedure, which have been described as being performed by a certain number of units or devices, can be performed by any other number of units or devices. For instance, these determinations and/or the control can be performed by a single processing unit. These determinations and/or the control of the system for performing the therapeutic procedure in accordance with the method for performing the therapeutic procedure can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to a system for performing a therapeutic procedure like a HDR brachytherapy. An elongate introduction element is introduced into a body, a temperature is determined along the introduction element, and it is determined which part of the introduction element is within the body based on the determined temperature. A therapeutic procedure is performed by using the introduction element depending on the determination which part of the introduction element is within the body. This can ensure that the therapeutic procedure is only performed within the body, thereby reducing the likelihood of involuntary affecting, for instance, a patient's outer skin, especially by ionizing radiation which may be used during a HDR brachytherapy.

The invention claimed is:

1. A system for performing a therapeutic procedure, wherein the system comprises:
    an elongate introduction element for being introduced into a body,
    a temperature determination unit for determining a temperature along the introduction element,
    an inner part determination unit for determining which part of the introduction element is within the body based on the determined temperature,
    a therapeutic procedure performing unit for performing the therapeutic procedure by using the introduction element depending on the determination which part of the introduction element is within the body such that the therapeutic procedure is performed only at a predetermined inner part of the introduction element, and
    a depth determination unit for determining the depth of the introduction element within the body based on the predetermined inner part of the introduction element, wherein the depth determination unit is further adapted to determine a deviation of the determined depth of the introduction element with a predefined depth and to indicate the deviation.

2. The system as defined in claim 1, wherein the introduction element is a catheter and wherein the therapeutic procedure performing unit comprises:
    a moving unit for moving a radiation source to a dwell position for treating the body at the dwell position within the catheter, and
    a brachytherapy control unit for controlling the moving unit such that the dwell position is within a part of the catheter which has been determined to be within the body.

3. The system as defined in claim 1, wherein the introduction element comprises an optical fiber for generating optical signals being indicative of the temperature along the introduction element and wherein the temperature determination unit is adapted to determine the temperature along the introduction element based on the generated optical signals.

4. The system as defined in claim 1, wherein the inner part determination unit is adapted to determine which part of the introduction element is within the body by determining an increase or decrease of the temperature along the introduction element.

5. The system as defined in claim 1, wherein the inner part determination unit is adapted to determine which part of the introduction element is within the body by modeling thermodynamic properties of the body and/or of the environment and/or of the introduction element and by using the determined temperature along the introduction element.

6. The system as defined in claim 1, wherein the system further comprises a target depth providing unit for providing a target depth of the introduction element and a guidance information generation unit for generating guidance information being indicative of a movement of the introduction element, which would allow the introduction element to reach the target depth, based on the provided target depth and the determined depth of the introduction element.

7. The system as defined in claim 1, wherein the system further comprises:
    a position determination unit for determining a position of the introduction element within the body,
    a body image providing unit for providing a body image, wherein the provided body image is registered with the determined position of the introduction element,
    an introduction element image generation unit for generating an introduction element image showing a representation of the introduction element within the body image based on the determined position of the introduction element within the body and the body image.

8. The system as defined in claim 7, wherein the introduction element image generation unit is configured to generate the introduction element image showing a representation of only a part of the introduction element which is within the body.

9. The system as defined in claim 7, wherein the introduction element comprises an optical shape sensing fiber for generating optical shape sensing signals being indicative of the position of the introduction element within the body and wherein the position determination unit is adapted to determine the position of the introduction element within the body based on the generated optical shape sensing signals.

10. The system as defined in claim 7, wherein the body image providing unit is adapted to indicate a position at which the introduction element is introduced into the body, relative to the provided body image and to register the body image with the position of the introduction element.

11. A computer program for performing a therapeutic procedure, the computer program comprising program code means for causing a system as defined in claim 1 to carry out the following steps, when the computer program is run on a computer controlling the system:

determining the temperature along an introduction element, which has been introduced into a body, determining which part of the introduction element is within the body based on the determined temperature, controlling the therapeutic procedure performing unit to perform the therapeutic procedure using only a part of the introduction element which has been introduced into the body.

12. A system for performing brachytherapy, the system comprising:
    a catheter configured for insertion into a patient, the catheter including an interior passage and an optical fiber configured to generate optical signals;
    a radiation source configured to move through the interior passage of the catheter; and,
    a computer processor configured to:
        determine temperatures along the catheter from the optical signals,
        from the determined temperatures, determine which part of the catheter is inserted in the patient, and determine at least one of a depth and/or a location of a predetermined inner part of the catheter inserted into the patient,
        control the radiation source to move continuously through the catheter interior passage without dwelling to a preselected dwell location along the catheter part in the predetermined inner part in the patient,
        determine a depth of the preselected dwell location based on the predetermined inner part of the catheter,
        determine a deviation of the determined depth with a predefined depth and indicate the deviation, and
        dwell the radiation source at the dwell location to perform the brachytherapy.

13. A therapy method comprising:
    identifying a target in a patient;
    inserting a catheter partially into the patient until a portion of the catheter is adjacent the target;
    measuring temperatures along the catheter;
    based on the measured temperatures, determining which part of the catheter is in the patient;
    continuously moving a therapeutic element through an insertion passage of the catheter until the therapeutic element is in the part of the catheter determined to be in the patient;
    determining a deviation between the portion of the catheter adjacent the target and the therapy element; and
    indicating the deviation.

14. The method as defined in claim 13, wherein the therapeutic element includes a radiation source.

15. The method according to claim 14, further including:
    moving the radiation source through the insertion passage minimizing the deviation; and
    stopping movement of the radiation source adjacent the target to perform radiation therapy.

16. The method as defined in claim 14, further including determining a depth of the radiation source within the patient.

* * * * *